United States Patent [19]

Obayashi et al.

[11] Patent Number: 5,458,877
[45] Date of Patent: * Oct. 17, 1995

[54] ANTIBACTERIAL AND ANTIPUPATION COMPOSITION

[75] Inventors: Hisashi Obayashi, Shiga; Yasuhiro Matsumura; Hiroyuki Takahata, both of Osaka, all of Japan

[73] Assignee: Takeda Garden Products Co., Ltd., Tokyo, Japan

[*] Notice: The portion of the term of this patent subsequent to Mar. 29, 2011 has been disclaimed.

[21] Appl. No.: 282,176

[22] Filed: Jul. 29, 1994

Related U.S. Application Data

[63] Continuation of Ser. No. 554,887, Jul. 20, 1990, abandoned.

[51] Int. Cl.$^6$ .......................... A01N 65/00; A61K 31/71; A61G 01/04
[52] U.S. Cl. ................................. 424/195.1; 424/78.08; 47/1.1; 47/9; 47/58; 47/59
[58] Field of Search ............................ 424/195.1, 78.08; 47/1.1, 9, 58, 59

[56] References Cited

U.S. PATENT DOCUMENTS

| | | | |
|---|---|---|---|
| 3,812,615 | 5/1974 | Jamison | 47/9 |
| 3,973,355 | 8/1976 | McKenzie | 47/37 |
| 4,071,973 | 2/1978 | Iizuka | 47/1.1 |
| 4,154,174 | 5/1979 | Rees | 47/58 |
| 4,250,662 | 2/1981 | Rees | 47/58 |
| 4,253,273 | 3/1981 | Rees | 47/58 |
| 4,707,176 | 11/1987 | Durham | 47/59 |
| 4,918,861 | 4/1990 | Carpenter | 47/59 |
| 4,932,156 | 6/1990 | Underwood | 47/9 |
| 4,959,926 | 10/1990 | Moffet, Jr. | 47/59 |
| 5,018,301 | 5/1991 | Kusakabe | 47/1.1 |
| 5,149,534 | 9/1992 | Obayashi et al. | 424/195.1 |
| 5,298,241 | 8/1994 | Obayashi et al. | 424/76.1 |

FOREIGN PATENT DOCUMENTS

| | | |
|---|---|---|
| 2-49516 | 2/1990 | Japan . |
| 2-49516 | 2/1990 | Japan . |
| 3019628 | 1/1991 | Japan . |

OTHER PUBLICATIONS

A. C. Bunt, "Modern Potting Composts,"© George Allen & Unwin Ltd. (1976).

Howard M. Resh, PhD., Hydroponic Food Production, A Definitive Guidebook for the Advanced Home Gardener and the Commercial Hydroponic Grower, 2d Ed., Woodbridge Press Pub. Co. (1981).

*Primary Examiner*—John W. Rollins
*Attorney, Agent, or Firm*—Jacobson, Price, Holman & Stern

[57] ABSTRACT

An antibacterial and anti-pupation composition which includes at least 60 weight % shredded cortex of Japanese cedar, shredded cortex of Japanese cypress, or a mixture thereof; and a nonionic or anionic surfactant in an amount sufficient to maintain the cortex of Japanese cedar or Japanese cypress water-permeable and water-retentive when dry.

20 Claims, No Drawings

ANTIBACTERIAL AND ANTIPUPATION COMPOSITION

This application is a continuation of U.S. patent application Ser. No. 07/554,887, filed Jul. 20, 1990, abandoned.

BACKGROUND OF THE INVENTION

1. Field of the Invention

The present invention relates to an antibacterial and antipupation composition for growing and cultivating plants.

2. Prior Art

Conventional artificial bed soils include dried sphagnum.

Sphagnum, a moss belonging to the family Sphagnaceae, has transparent cells of high water absorptivity, based on which it serves well as a bed soil material.

The prior art bed soil described above has the following drawbacks (1) through (5).

(1) Since sphagnum shows a high water retentivity (water retention ratio about 60% by volume), frequent rainfall or watering causes root rot in grown plants (particularly orchids) due to moisture damage associated with excess water retention.

(2) Since sphagnum is highly decomposable by bacteria, ammoniac nitrogen concentration increases significantly with time. It is therefore difficult to determine the appropriate amount of fertilizer to use, which uncertainty can easily lead to salt injury due to excess application, followed by poor growth of grown plants.

In addition, since sphagnum rots in at most one year, it must be renewed every year or slightly less, particularly in orchid cultivation.

(3) To avoid the wet injury and salt injury described above, water and fertilizer amounts must be strictly regulated at appropriate levels with the confirmation of water retention status and nutrient concentration status, which makes watering and fertilizer application management difficult.

(4) As stated above, since sphagnum is highly decomposable by bacteria, it loses its bed soil function with time. Continuous use for 2 to 3 years as bed soil material causes what is called injury by continuous cropping, in which it is almost impossible to grow plants.

Particularly in orchid cultivation, sphagnum must be renewed in about 1 year, as stated above.

(5) As stated above, since sphagnum is highly decomposable by bacteria, it changes to powder form after being used as bed soil material for 1 to 2 years, when it nourishes airborn weed seeds on bed soil surface and aids in their germination, easily leading to the occurrence of weeds.

It has long been desired that an artificial bed soil free of these drawbacks be developed, of a material whose water retentivity is appropriately low and whose bacterial decomposability is low.

Recently, a method has been proposed in which the cortex of Japanese cedar or Japanese cypress is cut into bed soil material form for use as such a material [Konnichi no Nogyo, Chemical Daily Press, April, 1989, pp. 110–114)].

However, even this type of artificial bed soil poses the following new problems (6) through (9).

(6) Since when dried, its surface becomes water repellent, water permeability and water retentivity are lost, which prevents the irrigation water from reaching the roots and causes the death of grown plants.

(7) Since drying must be prevented during cultivation to avoid the water repellency described above, watering must always be conducted before drying, which makes watering management troublesome.

(8) Since drying must be prevented even in the process of product distribution to avoid the water repellency described above, water must be supplemented in the process of distribution, as the case may be, which makes product management troublesome.

(9) Since the finished product must be kept water retaining, as stated above, product weight is increased, which is disadvantageous in transportation.

The object of the present invention is to provide an artificial bed soil free of wet injury, nutrient salt injury and injury by continuous cropping and capable of recovering or maintaining its water permeability and water retentivity even when once dried.

SUMMARY OF THE INVENTION

This invention relates to an antibacterial and antipupation composition useful as the following artificial bed soils:

(1) An artificial bed soil produced by the addition of a surfactant to the shredded cortex of Japanese cedar and/or Japanese cypress, namely, an artificial bed soil, which comprises (1) a surfactant and (2) the shredded cortex of Japanese cedar and/or Japanese cypress;

(2) An artificial bed soil characterized by the retention of said surfactant to porous grains, namely, an artificial bed soil wherein said surfactant is retained in porous grains;

(3) An artificial bed soil characterized by further including vermiculite;

(4) An artificial bed soil characterized by the use of vermiculite in place of the surfactant;

(5) An artificial bed soil characterized by the addition of a water-holding material;

(6) A mulching material comprising an artificial bed soil; and (7) A flower bed characterized in that an artificial bed soil is placed on a roof floor or veranda.

Accordingly, the present invention relates to an artificial bed soil comprising 1) shredded cortex of Japanese cedar and/or Japanese cypress and 2) a surfactant and/or vermiculite. The surfactant may be retained by adsorption to porous grains. In addition to these components 1) and 2), the artificial bed soil of the present invention may contain other components which can be used for plant cultivation such as 3) water retaining agents, 4) chemical fertilizers or organic manure, 5) herbal organic matter, 6) mineral powder, 7) synthetic fiber, 8) preservatives or antifungal agents, 9) systemic insecticides and 10) systemic fungicides.

The Japanese cedar and Japanese cypress mentioned above are exemplified by *Cryptomeria Japonica* and *Chamaecyparis obtusa*, respectively. Examples also include varieties thereof.

Shredded cortex of Japanese cedar or Japanese cypress can easily be produced by, for example, the method described in Japanese Patent Publication Open to Public Inspection No. 49516/1990 and the method in which bark removed by using a dry barker is directly shredded in a rotary mill. It is preferable to use shredded cortex of Japanese cedar or Japanese cypress after preparation into a feathery form.

The purpose of addition of a surfactant is to prevent the shredded cortex of Japanese cedar or Japanese cypress from drying to become water repellent and to recover water permeability and water retentivity in said shredded cortex that has become water repellent after drying.

Any surfactants can serve well. Particularly cationic surfactants, anionic surfactants and nonionic surfactants can be suitably used. But anionic surfactants and nonionic surfactants are more preferable.

Examples of cationic surfactants include
1. Lauryltrimethylammoniumchloride
2. Cetyltrimethylammoniumchloride
3. Stearyltrimethylammoniumchloride
4. Dilauryldimethylammoniumchloride
5. Distearyldimethylammoniumchloride
6. Lauryldihydroxyethylmethylammoniumchloride
7. Oleylbispolyoxyethylenemethylammoniumchloride
8. Stearlhydroxyethyldimethylammoniumchloride
9. Lauryldimethylbenzylammoniumchloride
10. Laurylaminopropyldimethylethylammoniumsulfate
11. Laurylaminopropyldimethylhydroxyethylammoniumperchlorate Examples of anionic surfactants include polyoxyethylene nonylphenyl ether sulfate ammonium salt, polyoxyethylene dinonylphenyl ether sulfate ammonium salt, polyoxyethylene distyrenated phenyl ether sulfate ammonium salt and polyoxyethylene synthetic alcohol sulfate ammonium salt. As specific commercial names thereof, mention may be made of RY-321, 335, 333 and 334, all produced by Matsumoto Yushi-Seiyaku Co., Ltd.

Examples of nonionic surfactants include polyoxyethylene nonylphenyl ether, polyoxyethylene bisalkylphenyl ether, polyoxyethylene styrenated phenyl ether, polyoxyethylene oleyl ether, polyoxyethylene castor oil and polyoxyethylene glycol oleate. As specific commercial names thereof, mention may be made of Penerol NP-2, Penerol BNP-20, Penerol SP-18, Actinol OL-6, Actinol CS-10 and Brian O-200, all produced by Matsumoto Yushi-Seiyaku Co., Ltd. And biodegradatinable surface active agent such as Sylvan T-20, Sylvan T-60, Sylvan T-80, Hymal F-3, Hymal F-5, Hymal F-7, Hymal F-9 can be listed, all produced by Matsumoto Yushi-Seiyaku Co., Ltd. But abiodegradable surface active agent is preferable.

It is preferable that the surfactant be formulated in a ratio of about 0.01 to 5.0% by weight, more preferably 0.05 to 1.0% by weight, to the total weight of the artificial bed soil.

This is because when the ratio is less than about 0.01% by weight, the surfactant sometimes fails to recover water permeability and water retentivity in the shredded cortex of Japanese cedar or Japanese cypress that has become water repellent after drying. On the other hand, when the ratio exceeds about 5.0% by weight, water permeability shows no further improvement, and it is feared that the large amount of surfactant may lead to poor growth of grown plants, and increase costs. In the range of from about 0.01 to 5.0% by weight, water permeability and other properties of the said shredded cortex can be recovered while ensuring the safety of grown plants and economic cost performance. Further, the shredded cortex of Japanese cedar or Japanese cypress is prevented from becoming water repellent by drying, with the surfactant's effect better ensured in the range of from about 0.05 to 1.0% by weight.

Surfactant may be retained by adsorption to porous grains in the artificial bed soil of the present invention.

The reason why it is preferable to retain surfactant by adsorption to porous grains is to prevent early run-off of the surfactant from bed soil, keeping the surfactant in the bed soil for a longer time and ensuring recovery of water permeability and other properties in the shredded cortex described above for a longer time.

Examples of porous grains which serve well in the artificial bed soil of the present invention include grains having a diameter of about 0.1 to 10 mm such as those of pumice, silica gel, diatomaceous earth, zeolite, granular concrete, gypsum, colloidal silicic acid, crushed stone, coconut shell, mortar, rice husk, silica, slug, cement, perlite, sponge and polystyrene.

It is preferable that these porous grains be formulated in a ratio of about 0.1 to 50% by weight, more preferably about 0.5 to 10% by weight, to the total weight of the artificial bed soil.

A surfactant can easily be adsorbed to porous grains usually by spraying or pouring the surfactant while stirring the porous grains.

The adsorption ratio of surfactant to porous grains is normally about 10 to 50% by weight, and the surfactant can be used as adsorbed in this range.

Vermiculite may be further included or used in place of surfactant in the artificial bed soil of the present invention.

The reason why vermiculite is used is that vermiculite can exist in dispersion in the shredded cortex of Japanese cedar or Japanese cypress that has become water repellent after drying, and forms water paths inside the shredded cortex of Japanese cedar or Japanese cypress by sequentially transferring moisture by its own high water permeability, though, unlike a surfactant, it cannot cause recovery of water permeability and other properties in the shredded cortex of Japanese cedar or Japanese cypress that has become water repellent.

It is preferable that vermiculite be formulated in a ratio of about 5 to 40% by weight, more preferably about 15 to 35% by weight, to the total weight of bed soil material.

This is because when the ratio is less than about 5% by weight, vermiculite sometimes fails to form sufficient water paths. On the other hand, when the ratio exceeds about 40% by weight, further improvement in water permeability is unnecessary, and the specific gravity of the bed soil increases, causing inconveniences in transportation, etc., and cost increases. In the range of from about 5 to 40% by weight, water permeability can be maintained while ensuring weight reduction in bed soil and economic cost performance, with the vermiculite's effect better ensured in the range of from about 15 to 35% by weight.

A water-holding material may be added to the artificial bed soil of the present invention.

The reason for adding a water-holding material is to keep the shredded cortex of Japanese cedar or Japanese cypress in a wet status for a long time by its own high water retentivity, and minimize its water repellency after drying.

Examples of water-holding materials include starch/acryl polymers, sodium polyacrylate polymers, vinyl acrylate alcohol polymers, methyl acrylate/vinyl acetate copolymers, polyacrylic acid crosslinked polymers, polyvinyl alcohol/acryl ester polymers, modified polyvinyl alcohol polymers, carboxymethylcellulose crosslinking products, specially treated acrylonitrile polymers, dissolving pulp polymers and sodium polyacrylate polymers. As specific commercial names, mention may be made of Sanwet IM300 (produced by Sanyo Chemical Industries, Ltd.), WAS (produced by Nichiden Kogyo), Sumikagel and Igetagel (produced by Sumitomo Chemical Co., Ltd.), Wondergel (produced by Kao Corporation), Aquakeep (produced by Seitetsu Kagaku Co., Ltd.), KI Gel (produced by Kuraray Isoprene Chemical), Especlan Seal (produced by Nippon Exlan), KP Series (produced by Japan Vilene Co., Ltd.), Kikkolate SC (produced by Nichirin Kagaku), Aquaprene (produced by Meisei Kagaku Kogyo), Nonsweat (produced by Henkel Japan) and Lion Polymer (produced by Lion Corporation).

It is preferable that the water-holding material be formulated in a ratio of about 0.01 to 3.0% by weight as active ingredient, more preferably about 0.05 to 1.0% by weight, to the total quantity of bed soil.

This is because when the ratio is less than about 0.01% by weight, the water-holding material holds only a small amount of water and sometimes fails to keep the shredded cortex of Japanese cedar or Japanese cypress wet for a long time. On the other hand, when the ratio exceeds about 3.0% by weight, excess water retention may cause root rot in orchids, etc. and cost increases. In the range of from about 0.01 to 3.0% by weight, the water-holding material can keep the said shredded cortex wet for a long time while ensuring the safety of grown plants, with its effect better ensured in the range of from about 0.05 to 1.0% by weight.

Further, if desired, chemical fertilizer, organic manure, herbal organic matter, mineral powder, synthetic fiber, preservatives or antifungal agents, systemic insecticide, systemic fungicide or the like may be added to the artificial bed soil of the present invention.

Listed as examples of the chemical fertilizers and organic manure are IBDU® (Mitsubishi Kasei), AIDE concentrate for flower use (Takeda Engei K.K), organic AIDE (Taki Chemical Co., Ltd.) or the like. But slow-release fertilizer is preferable. Although the amount to be used cannot be specifically mentioned, it is normally about 0.1 to 10%, preferably about 0.5 to 5%, of the amount of the finished artificial bed soil of the present invention.

Herbal organic matter means raw materials for Chinese crude drugs such as antyusan, heiisan, rhubarb and glycyrrhiza. Examples of such raw materials include medicinal plants such as rhubarb, licorice, Chinese peony, ginger and Atractylodes laucea, extract residues or processed products thereof. Preferable processed products include excrement from earthworms fed with these extract residues and compost prepared from these extract residues. An example of readily available herbal organic matter is "Medical-compo," produced by Karugen K.K., Japan. It is normally used in a ratio of about 1 to 50%, preferably about 5 to 30%, of the amount of the finished artificial bed soil of the present invention, although the amount to be used cannot be specifically mentioned.

To increase the specific gravity of the artificial soil, mineral powder may be formulated therein.

Examples of minerals include clay, talc and zeolite, with preference given to fine grains thereof. Although the amount of these materials used cannot be generally specified, it is normally about 5 to 80%, preferably about 15 to 30%, of the amount of the finished artificial bed soil of the present invention.

The present inventors discovered the fact that formulating synthetic fiber in the artificial bed soil of the present invention suppresses fungal occurrence.

Examples of synthetic fiber include polyester, nylon and polyethylene in a dust or shredded form. Although it is impossible to generally specify the amount of its use, it is normally used in a ratio of about 0.01 to 30%, preferably about 0.1 to 10%, to the amount of the finished artificial bed soil of the present invention.

Also, the artificial bed soil of the present invention may be formulated with preservative antifungal agents, preferably having no significant toxicity to animals and plants, e.g. Coatcide D®, Coatcide SP®, Coatcide 55D®, SLAOFF 620, SLAOFF 72N (Takeda Chemical Industries Ltd.), each of which mainly comprises methyl-2-benzimidazoyl carbamate (MBC). Although the amount to be used cannot be specifically mentioned, it is normally about 0.01 to 1.0%, preferably about 0.05 to 0.5% of the amount of the finished artificial bed soil of the present invention.

Examples of the systemic insecticide are Ortholane (chemical name: O,S-dimethyl N acetyl phosphoramido thioate) and Dipterex (chemical name: dimethyl(2,2,2-trichloro-1-hydroxyethyl phosphonate). Examples of the systemic fungicide are a Wettable powder contained 50% Benomilu (chemical name: methyl 1-(butyl carbamoyl)-2-benzimidazoyl carbamate) [Benlate Wettable powder (Takeda Garden Products), and a Emulsifiable Concentrate containing 15.0% Triforine Saprol (Takeda Garden Products)]. Although the amount to be used cannot be specifically mentioned, it is about 0.05 to 5%, preferably about 0.1 to 1% of the amount of the finished artificial bed soil of the present invention.

The artificial bed soil of the present invention may be colored with a pigment, a dye, etc.

Coloring can easily be achieved by covering the surface of the artificial bed soil with an ordinary coat-forming component or adhesive component containing a pigment or a dye. It is preferable to coat the surface of the artificial bed soil with a dry mixture prepared by mixing a resin with a pigment or a dye, followed by spraying and drying over the artificial bed soil, which is not liable to discoloration.

Examples of resins include vinyl acetate, vinyl acetate copolymers and other ordinary coat-forming components or adhesive components, i.e., 1) synthetic resins such as phenol resin, alkyd resin, vinyl chloride resin, epoxy resin and silicone resin and 2) natural drying oils such as linseed oil and tung oil and natural resins such as copal and rosin, with preference given to vinyl acetate emulsion.

Although it is impossible to generally specify the amount of use of these resins, they are normally used in a ratio of about 0.01 to 3.0%, preferably 0.05 to 1.0%, to the finished artificial bed soil of the present invention.

Any ordinary pigment, whether organic or inorganic, can be used, and any color is acceptable, including blue, green, yellow, orange, red and white. Examples of pigments which can serve well include copper phthalocyanine blue for blue color, copper phthalocyanine green for green color, bisazo pigments for yellow color, insoluble monoazo pigments for orange color, insoluble monoazo pigments for red color and condensation azo pigments, quinacridone pigments and azo pigments.

Any dye can be used, including natural dyes such as carotinoids, porphyrins and chlorophylis and synthetic dyes such as tar dyes.

Although it is impossible to generally specify the amount of use of these pigments and dyes, they are normally used in a ratio of about 0.05 to 3.0%, preferably 0.1 to 1.0%, to the finished artificial bed soil of the present invention.

The artificial bed soil of the present invention is easily produced by mixing, preferably homogeneously, the necessary components by a method known per se.

A mode of preferred use of the artificial bed soil of the present invention is as follows: For example, when it is used as a seeding bed, seeds are placed on the artificial bed soil of the present invention or a mixture thereof with ordinary soil or fertilizer, and the surface is covered with the artificial bed soil of the present invention. Thus, if a weed seed comes onto the artificial bed soil, it will not enter into the artificial bed soil but remain on the surface. In addition, since the surface of the artificial bed soil is dry, the weed seed cannot germinate.

Also, the artificial bed soil of the present invention has an antifrost effect, a warming effect and a water retaining effect as well as the above-mentioned weed controlling effect, it can serve as a mulching material (straw bedding substitute) to prevent, for example, frost injury on shallow-rooted plants.

Moreover, since the artificial bed soil of the present invention is light, it is easily portable and can be used as a bed soil for gardening on roof floor or veranda.

Furthermore, a fertilizer etc. may be formulated in the artificial bed soil of the present invention to promote plant growth.

EFFECTS OF THE INVENTION

The artificial bed soil of the present invention presents the following effects (1) through (12):

(1) Since the water retentivity of the shredded cortex of Japanese cedar or Japanese cypress is appropriately low (water content is about 30% by volume), even when rainfall or watering is frequent, there is litte fear of wet injury due to excess water retention; thus root rot in grown plants (particularly orchids) is effectively prevented.

(2) The shredded cortex of Japanese cedar or Japanese cypress is almost undecomposable by bacteria, enduring long-term use for more than 10 years. Also, since it shows little time-related change in ammoniac nitrogen concentration, it is easy to determine the appropriate fertilizer amount, and there is little fear of salt injury due to excess nutrition; poor growth of grown plants is thus efficiently prevented.

(3) Watering and fertilizer application management is easy, since excess water retention is not caused even by frequent rainfall or watering, and it is easy to determine an appropriate fertilizer amount as stated above.

(4) Since the shredded cortex of Japanese cedar or Japanese cypress is not easily decomposable by bacteria as stated above, its bed soil function does not decrease with time, thus causing no injury by continuous cropping, in which plant cultivation becomes almost impossible after 2 to 3 years.

(5) Since the shredded cortex of Japanese cedar or Japanese cypress is not easily decomposable by bacteria as stated above, its shape remains unchanged; therefore, it is difficult for airborn weed seeds to enter into the surface of the bed soil, the weed seeds become dry immediately and fail to germinate, and the occurrence of weeds is prevented.

(6) Even when the surface of the shredded cortex of Japanese cedar or Japanese cypress becomes water repellent after drying, surface wettability is increased by the surfactant in response to water supply by rainfall or watering, and thus it regains water permeability and water retentivity by water absorption in its texture.

Therefore, irrigation water can reliably reach roots, thus eliminating worry about the death of grown plants.

(7) Water permeation is ensured even when the surface of the shredded cortex of Japanese cedar or Japanese cypress becomes dry during cultivation; it is unnecessary to always water before drying with confirmation of water retention status; thus watering management is easy.

(8) Since it is unnecessary to avoid drying, water supplementation is unnecessary in the process of product distribution; thus product management is easy.

(9) Since the finished product can be obtained dry, product weight can be reduced for convenience in transportation.

(10) The surfactant is gradually released from porous grains, thus ensuring the recovery of water permeability and other properties of the shredded cortex of Japanese cedar or Japanese cypress.

(11) Even when the shredded cortex of Japanese cedar or Japanese cypress becomes water repellent after drying, water permeation is ensured through the water paths formed by vermiculite, thus not causing the death of grown plants.

(12) The water retentivity of the water-holding material aids the shredded cortex of Japanese cedar or Japanese cypress in retaining a large amount of water for a long time, thus ensuring water supply to grown plants.

The present inventors discovered the fact that the artificial bed soil of the present invention has the following effects (13), (14) and (15).

(13) Since the artificial bed soil of the present invention has a thermoinsulating effect, roof floor overheat is prevented and room temperature increase in the rooms below the roof floor is suppressed in summer when it is used as a bed soil for roof floor gardening. In winter, it serves well to keep rooms warm.

(14) Since the artificial bed soil of the present invention has an antifrost effect, frost injury on cultivated plants (particularly shallow-rooted plants) is prevented.

(15) Since the artificial bed soil of the present invention has a pupation preventing effect and an antibacterial effect, it permits agrichemical-free cultivation. For example, since house flies are controlled, the artificial bed soil of the present invention is hygienically favorable for house gardening. Lawn death may occur due to root eating by the Japanese beetle. Since the artificial bed soil of the present invention controls the Japanese beetle, it is suitable to lawn growing, and is conducive to mitigation of the current social problem of agrichemical use in golf links. The artificial bed soil of the present invention also permits agrichemical-free cultivation of herbs and other healthful plants.

To substantiate the effects described above, the present invention is hereinafter described in more detail by means of the following working examples and test examples.

Examples 1 through 5

A feathery preparation obtained by cutting the cortex of Japanese cedar into a feathery form and another feathery preparation obtained by treating the cortex of Japanese cypress in the same manner as above, were mixed uniformly in a ratio of 1 to 1. This mixture was formulated with RY-321 (polyoxyethylene-(6)-nonylphenyl ether sulfate ammonium salt), produced by Matsumoto Yushi-Seiyaku Co., Ltd., in ratios shown in Table 1 to yield artificial bed soils.

As shown in Table 1, RY-321 was formulated in a ratio of 0.01% by weight to the total weight of finished artificial bed soil for Example 1, in a ratio of 0.05% by weight for Example 2, in a ratio of 1.0% by weight for Example 3, in a ratio of 3.0% by weight for Example 4, and in a ratio of 5.0% by weight for Example 5.

Examples 6 through 10

A feathery preparation obtained by cutting the cortex of Japanese cedar into a feathery form and another feathery preparation obtained by treating the cortex of Japanese cypress in the same manner as above, were mixed uniformly in a ratio of 1 to 1. This mixture was formulated with vermiculite in ratios shown in Table 2 to yield artificial bed soils.

As shown in Table 2, vermiculite was formulated in a ratio of 5% by weight to the total weight of finished artificial bed soil for Example 6, in a ratio of 15% by weight for Example 7, in a ratio of 25% by weight for Example 8, in a ratio of 35% by weight for Example 9, and in a ratio of 40% by weight for Example 10.

Examples 11 through 15

A feathery preparation obtained by cutting the cortex of Japanese cedar into a feathery form and another feathery preparation obtained by treating the cortex of Japanese cypress in the same manner as above, were mixed uniformly in a ratio of 1 to 1. This mixture was formulated with Hymal F-7 (polyoxyethylene-(7)-secondaryalkyl ether), produced by Matsumoto Yushi-Seiyaku Co., Ltd., in ratios shown in Table 2 to yield artificial bed soils.

As shown in Table 2, Hymal F-7 was formulated in a ratio of 0.01% by weight to the total weight of finished artificial bed soil for Example 11, in a ratio of 0.05% by weight for Example 12, in a ratio of 1.0% by weight for Example 13, in a ratio of 3.0% by weight for Example 14, and in a ratio of 5.0% by weight for Example 15.

Example 16

While mixing 50 parts of shredded cortex of Japanese cedar and 46 parts of shredded cortex of Japanese cypress, 2 parts of silica, 1 part of coconut shell and 1 part of perlite were added, and 0.07 part of Hymal F-7 and 0.005 part of Hana-Kojyo original solution (Takeda Garden Products) were sprayed to yield an artificial bed soil.

Example 17

While mixing 85 parts of shredded cortex of Japanese cedar and 10 parts of shredded cortex of Japanese cypress, 1 part of polystyrene, 3 parts of cement and 1 part of silica were added, and 0.07 part of Hymal F-7 and 0.005 part of Hana-Kojyo original solution (Takeda Garden Products) were sprayed to yield an artificial bed soil.

Example 18

While mixing 95 parts of shredded cortex of Japanese cedar and 1 part of shredded cortex of Japanese cypress, 1 part of natural pumice, 2 parts of cement and 1 part of rice husk were added, and 0.07 part of Hymal F-7 and 0.005 part of Hana-Kojyo original solution (Takeda Garden Products) were sprayed to yield an artificial bed soil.

Example 19

While mixing 90 parts of shredded cortex of Japanese cedar and 5 parts of shredded cortex of Japanese cypress, 2.5 parts of vermiculite, 1 part of natural pumica and 1.5 parts of foaming cement were added, and 0.07 part of Hymal F-7 and 0.005 part of Hana-Kojyo original solution (Takeda Garden Products) were sprayed to yield an artificial bed soil.

Example 20

While mixing 84.5 parts of shredded cortex of Japanese cedar and 5 parts of shredded cortex of Japanese cypress, 8 parts of vermiculite, 1 part of natural pumica and 1.5 parts of foaming cement were added, and 0.07 part of Hymal F-7 and 0.005 part of Hana-Kojyo original solution (Takeda Garden Products) were sprayed to yield an artificial bed soil.

Example 21

91.5 parts of shredded cortex of Japanese cedar was mixed with 5 parts of peat moss, 3 parts of Biocompo (produced by Tainaka Ryuko) and 0.5 part of cement, and 0.10 part of Hymal F-9 and 0.010 part of Hana-Kojyo original solution (Takeda Garden Products) were sprayed to yield an artificial bed soil.

Example 22

While mixing 90.5 parts of shredded cortex of Japanese cedar and 5 parts of shredded cortex of Japanese cypress, 2 parts of Biocompo, 1.5 parts of cement and 1 part of natural pumica were added, and 0.07 part of Hymal F-7 and 0.005 part of Hana-Kojyo original solution (Takeda Garden Products) were sprayed to yield an artificial bed soil.

Example 23

While mixing 90 parts of shredded cortex of Japanese cedar and 3 parts of shredded cortex of Japanese cypress, 2 parts of Igetagel Soil® (produced by Sumitomo Chemical), 2.5 parts of Biocompo (produced by Tainaka Ryuko) and 2.5 parts of Potlight (produced by ONODA ALL Co. Ltd.) were added, and 0.07 part of Hymal F-7 and 0.005 part of Hana-Kojyo original solution (Takeda Garden Products) were sprayed to yield an artificial bed soil.

Example 24

While mixing 90.6 parts of shredded cortex of Japanese cedar and 6 parts of shredded cortex of Japanese cypress, 1 part of Igetagel Soil®, 0.9 part of mortar and 1.5 parts of silica were added, and 0.07 part of Hymal F-9 and 0.005 part of Hana-Kojyo original solution (Takeda Garden Products) were sprayed to yield an artificial bed soil.

Example 25

While mixing 89.5 parts of shredded cortex of Japanese cedar and 2 parts of shredded cortex of Japanese cypress, 3.5 parts of crushed stone, 2 parts of foaming cement and 3 parts of herbal organic matter were added, and 0.07 part of Hymal F-7 and 0.005 part of Hana-Kojyo original solution (Takeda Garden Products) were sprayed to yield an artificial bed soil.

Test Example 1

As shown in Tables 1 and 2, the artificial bed soils obtained in Examples 1 through 5 and 11 through 15 above were examined for water permeability and plant growth (watering was conducted every three days) in comparison with an artificial bed soil not formulated with a surfactant for Test Example 1.

Testing was conducted by packing a petri dish with each of the artificial bed soils of Examples 1 through 5 and 11 through 15 and Test Example 1 to a depth of 2 cm and dripping water on the surface thereof from above.

Water permeability was rated as effective when the dripped water was immediately absorbed via the surface of the artificial bed soil and as noneffective when the dripped water was not immediately absorbed.

The results of assessment are shown in Tables 1 and 2.

As is evident from Table 1, effective water permeability was obtained when RY-321 or Hymal F-7 was formulated in ratios above 0.01% by weight.

Also, as stated above, when the ratio exceeds 5.0% by weight, no further improvement occurs in water permeability. On the contrary, it is feared that a large amount of surfactant may hamper the growth of grown plants, and result in cost increases.

For these reasons, it is evident that in the range of from 0.01 to 5.0% by weight, water permeability and other properties of the feathery preparation can be recovered while maintaining safety of grown plants and economic cost performance. Particularly the range of from 0.05 to 1.0% by weight was found most preferable.

Test Example 2

As shown in Table 3, the artificial bed soils obtained in Examples 6 through 10 above were examined for water permeability in comparison with an artificial bed soil not formulated with vermiculite for Test Example 2.

Testing was conducted and water permeability was rated in the same manner as in Test Example 1 described above.

The results of assessment are shown in Table 3.

As is evident from Table 3, effective water permeability was obtained when vermiculite was formulated in ratios above 5% by weight.

Also, as stated above, even when the ratio exceeds. 40% by weight, further improvement in water permeability is unnecessary for bed soil. On the contrary, transportation, etc. become difficult due to increase in the specific gravity of bed soil and cost increases.

For these reasons, it is evident that in the range of from 5 to 40% by weight, water permeability can be maintained while ensuring weight reduction of bed soil and economic cost performance, with its effect better ensured in the range of from 15 to 35% by weight.

TABLE 1

|  | Amount of RY-321 Formulated | Water Permeability | Miniature Rose Growth |
| --- | --- | --- | --- |
| Example 1 | 0.01 | o | o |
| Example 2 | 0.05 | o | o |
| Example 3 | 1.0 | o | o |
| Example 4 | 3.0 | o | o |
| Example 5 | 5.0 | o | o |
| Comparative Example 1 | 0 | X | X(death) |

TABLE 2

|  | Amount of Hymal F-7 Formulated | Water Permeability | Miniature Rose Growth |
| --- | --- | --- | --- |
| Example 11 | 0.01 | o | o |
| Example 12 | 0.05 | o | o |
| Example 13 | 1.0 | o | o |
| Example 14 | 3.0 | o | o |
| Example 15 | 5.0 | o | o |
| Comparative Example 1 | 0 | X | X(death) |

TABLE 3

|  | Amount of Vermiculite Formulated | Water Permeability | Tomato Growth |
| --- | --- | --- | --- |
| Example 6 | 5 | o | o |
| Example 7 | 15 | o | o |
| Example 8 | 25 | o | o |

TABLE 3-continued

|  | Amount of Vermiculite Formulated | Water Permeability | Tomato Growth |
| --- | --- | --- | --- |
| Example 9 | 35 | o | o |
| Example 10 | 40 | o | o |
| Comparative Example 2 | 0 | X | X(death) |

In Tables 1, 2 and 3, figures for the amount of RY-321, Hymal F-7 and vermiculite formulated are shown in % by weight; of the symbols for water permeability assessment, o indicates effective and x indicates noneffective.

Test Example 3 Thermoinsulation Test

The artificial bed soil of Example 2 and thermoinsulating building material asbestos for Comparison Example were heated, and the surface temperature etc. of each test piece was measured and their thermal conductivity was calculated. Measurements were made in accordance with JIS A 1412–1989 "Methods of Determination of Thermal Conductivity of Heat Retaining Materials," 5.2 Plate Comparison Method.

The results of calculation are given in Table 4.

TABLE 4

|  | Test Piece Average Temperature (°C.) | Thermal Conductivity $\lambda\theta$ (kcal/mh°C.) |
| --- | --- | --- |
| Example 2 | 20.0 | 0.096 |
| Comparison Example | 20.0 | 0.13 |

As is evident from Table 4, the artificial bed soil of the present invention surpasses thermoinsulating building material asbestos in thermoinsulating effect.

Test Example 4 Weed Control Test

The artificial bed soil of Example 2 and a commercially available flower soil (tradename: Tosho Planter Bed Soil) for Comparison Example were each placed in planters and kept standing outdoors for 6 months, and then examined for weeds.

The results are shown in Table 5.

TABLE 5

Unit: pc.

| Treatment Plot | Weed Species | | | | |
| --- | --- | --- | --- | --- | --- |
|  | Canadian Fleabane | Common Purslane | Chickweed | Goosegrass | Others |
| Example 2 | 2 | 0 | 0 | 0 | 3 |
| Comparison Example | 9 | 14 | 25 | 5 | 12 |

As is evident from Table 5, almost no weeds occurred in the artificial bed soil of the present invention while a large number of weeds occurred in the commercially available flower soil.

Test Example 5 House Fly Larva Growth Suppression Test

A 200 ml portion of each of the artificial bed soil of the present invention, natural field soil collected from Kyoto for Comparison Example 1 and leaf mould collected from Osaka was placed in a 1-liter beaker. In each beaker, 50 house fly larvae at the second stage in age were placed, and the beaker was covered with filter paper. The beakers were kept standing in a constant temperature chamber at 25° C. for 14 days with 5 ml of water added once daily. Then, the pupae and the emerged adults were counted.

The results are shown in Table 6.

TABLE 6

|  | Number of Pupae (A) | Number of Emerged Adults (B) | Occurrence Suppression Rate (%) |
|---|---|---|---|
| Example 1 | 1 | 0 | 98.0 |
| Example 2 | 0 | 0 | 100.0 |
| Example 7 | 3 | 0 | 94.0 |
| Example 8 | 5 | 0 | 90.0 |
| Example 10 | 3 | 0 | 94.0 |
| Example 16 | 0 | 3 | 94.0 |
| Example 18 | 0 | 1 | 98.0 |
| Example 20 | 0 | 0 | 100.0 |
| Exampel 21 | 0 | 0 | 100.0 |
| Example 24 | 2 | 2 | 92.0 |
| Example 25 | 4 | 2 | 88.0 |
| Comparison Example 1 | 3 | 42 | 10.0 |
| Comparison Example 2 | 7 | 41 | 4.0 |

Note: Occurrence suppression rate(%) = 100 − [(A + B)/50] × 100

As is evident from Table 6, the artificial bed soil of the present invention significantly suppressed the occurrence of house flies.

Test Example 6 Cucumber Damping-off Control Test

Subject Plant and Pathogens

The cucumber (variety: Yotsuba) was used for the test. The inoculant pathogens were *Rhizoctonia solani* (Ibaraki Agricultural Experimental Station, No. 63) cultured in rice husk medium at 28° C. for 7 days and *Fusarium oxysporum* f. sp. *cucumerinum* (Shinsyu University, SUF 359) cultured in corn medium at 28° C. for 14 days.

Method

° Testing with *Rhizoctonia solani*

Onto the surface (3 cm) of each of the artificial bed soil of the present invention, natural field soil collected from Kyoto for Comparison Example 1 and natural field soil collected from Tochigi for Comparison Example 2, 1.0 g, 2.0 g or 3.0 g per pot of a rice husk medium containing grown bacterial cells was added for inoculation. The pots were kept in a moisturized chamber at 28° C. for 1 day. Then, 10 cucumber seeds per pot were seeded and nursed in a green house for 10 days, followed by examination.

° Testing with *Fusarium oxysporum*

To a medium cotaining grown bacterial cells, a two-fold volume of corn flouer was added, and this mixture was crushed in a mechanical juicer. This product was mixed for inoculation in the entire portion of each of the artificial bed soil of the present invention, natural field soil collected from Kyoto for Comparison Example 1 and natural field soil collected from Tochigi for Comparison Example 2. The pots were kept in a moisturized chamber at 28° C. for 1 day. Then, 10 cucumber seeds per pot were seeded and nursed in a green house for 14 days, followed by examination.

Examination and Evaluation

° Examination and evaluation for *Rhizoctonia solani*

Ten days after seeding, each plant was examined and evaluated on the basis of the following criteria:
Index (I)
0: Normal
0.5: Slight disease symptom in the root portion
1: No disease symptom in the top, but onset found in the ground and root portions
2: Onset observed in the top, with initial damping-off symptom
3: No growth due to injury upon germination or in initial stage Judgment: Degree of injury (%)=ΣnI/(3×number of plants) where n represents the number of plants assessed for index I.

° Examination and evaluation for *Fusarium oxysporum*

Fourteen days after seeding, each plant was examined and evaluated on the basis of the following criteria:
Index (I)
0: Normal
0.5: Normal appearance, but slight browning in the vessels
1: Growth delay and severe browning in the vessels
2: Severe growth delay and clear Fusarium wilt
3: Complete damping-off Judgment: Degree of injury (%)=ΣnI/(3×number of plants) where n represents the number of plants assessed for index I.

The results are shown in Table 7.

TABLE 7

| Example Number | Amount of Medium Containing Bacterial Cells Applied | Degree of Injury (%) | |
|---|---|---|---|
| | | Rhizoctonia | Fusarium Oxysporum |
| 1 | 1.0 | 19.6 | 31.7 |
| | 2.0 | 15.0 | 25.4 |
| | 3.0 | 13.8 | 27.8 |
| 10 | 1.0 | 12.5 | 25.5 |
| | 2.0 | 16.8 | 27.8 |
| | 3.0 | 18.9 | 24.1 |
| 16 | 1.0 | 18.3 | 30.2 |
| | 2.0 | 15.0 | 24.7 |
| | 3.0 | 16.9 | 25.0 |
| 20 | 1.0 | 7.0 | 18.6 |
| | 2.0 | 8.4 | 25.5 |
| | 3.0 | 8.3 | 29.0 |
| 25 | 1.0 | 14.3 | 26.5 |
| | 2.0 | 17.1 | 28.8 |
| | 3.0 | 23.4 | 33.0 |
| Natural field soil-K (collected from Kyoto) | 1.0 | 46.3 | 64.2 |
| | 2.0 | 52.4 | 75.8 |
| | 3.0 | 51.6 | 81.7 |
| Natural field soil-T (collected from Tochigi) | 1.0 | 50.2 | 77.2 |
| | 2.0 | 57.7 | 83.6 |
| | 3.0 | 60.8 | 89.5 |

These results show that the artificial bed soil of the present invention much surpasses known artificial bed soils used in the Comparative Examples, with respect to plant growth and water permeability, and further suppression of generation of weed and harmful insects.

What is claimed is:

1. An antibacterial and anti-pupation composition comprising:

(a) at least 60 weight % shredded cortex of Japanese cedar, shredded cortex of Japanese cypress, or a mixture thereof; and (b) a nonionic or anionic surfactant in an amount sufficient to maintain the cortex of Japanese cedar or Japanese cypress water-permeable and water-retentive when dry.

2. The composition of claim 1 further comprising porous grains, wherein said surfactant is retained in said porous grains.

3. The composition of claim 2 wherein said porous grains have a diameter of about 0.1 to 10 mm.

4. The composition of claim 2 wherein said porous grains are present in an amount of 0.1 to 50 percent by weight based on the total weight of the composition.

5. The composition of claim 2 further comprising vermiculite.

6. The composition of claim 1 further comprising vermiculite.

7. The composition of claim 6 wherein said vermiculite is present in an amount of 5 to 40 percent by weight based on the total weight of the composition.

8. The composition of claim 6 further comprising a water-holding polymer.

9. The composition of claim 1 further comprising a water-holding polymer.

10. The composition of claim 9 wherein said water-holding polymer is present in an amount of 0.1 to 3.0 percent by weight based on the total weight of the composition.

11. The composition of claim 10 wherein said water-holding polymer is selected from the group consisting of starch/acryl polymers, sodium polyacrylate polymers, vinyl acrylate alcohol polymers, methyl acrylate/vinyl acetate copolymers, polyacrylic acid crosslinked polymers, polyvinyl alcohol/acryl ester polymers, modified polyvinyl alcohol polymers, carboxymethylcellulose crosslinking polymers, specially treated acrylonitrile polymers and dissolving pulp polymers.

12. The composition of claim 2 further comprising a water-holding polymer.

13. The composition of claim 1 wherein said surfactant is present in an amount of 0.01 to 5.0 percent by weight based on the total weight of the composition.

14. The composition of claim 13 further comprising vermiculite present in an amount of 5 to 40 percent by weight based on the total weight of the composition and a water-holding polymer present in an amount of 0.1 to 3.0 percent by weight based on the total weight of the composition.

15. The composition of claim 1 further comprising a mineral powder.

16. The composition of claim 1 further comprising a fertilizer.

17. The composition of claim 1 further comprising a herbal organic matter.

18. The composition of claim 1 further comprising synthetic fibers selected from the group consisting of polyester, nylon and polyethylene.

19. The composition of claim 1 further comprising a systemic insecticide or a systemic fungicide.

20. An antibacterial and anti-pupation composition comprising vermiculite and shredded cortex of Japanese cedar, shredded cortex of Japanese cypress, or a mixture thereof.

* * * * *